US011001546B2

(12) United States Patent
Deur-Bert et al.

(10) Patent No.: US 11,001,546 B2
(45) Date of Patent: May 11, 2021

(54) TERNARY AZEOTROPIC OR QUASI-AZEOTROPIC COMPOSITION COMPRISING HF, 2,3,3,3-TETRAFLUOROPROPENE AND 1,1,1,2,2-PENTAFLUOROPROPANE

(71) Applicant: Arkema France, Colombes (FR)

(72) Inventors: Dominique Deur-Bert, Pierre-Benite (FR); Laurent Wendlinger, Pierre-Benite (FR); Béatrice Berger, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/965,638

(22) PCT Filed: Feb. 1, 2019

(86) PCT No.: PCT/FR2019/050229
§ 371 (c)(1),
(2) Date: Jul. 29, 2020

(87) PCT Pub. No.: WO2019/150052
PCT Pub. Date: Aug. 8, 2019

(65) Prior Publication Data
US 2021/0017107 A1    Jan. 21, 2021

(30) Foreign Application Priority Data

Feb. 5, 2018 (FR) ........................ 1850925

(51) Int. Cl.
*C07C 21/18* (2006.01)
*C07C 17/383* (2006.01)

(52) U.S. Cl.
CPC ............ *C07C 21/18* (2013.01); *C07C 17/383* (2013.01)

(58) Field of Classification Search
CPC ....... C07C 21/18; C07C 17/383; C09K 5/045; C09K 2205/22; C09K 2205/32; C09K 2205/126; C09K 2205/122
See application file for complete search history.

(56) References Cited

U.S. PATENT DOCUMENTS

| 6,013,846 | A | 1/2000 | Wismer et al. |
|---|---|---|---|
| 7,476,771 | B2 | 1/2009 | Miller et al. |
| 8,070,977 | B2 | 12/2011 | Rached |
| 8,075,798 | B2 | 12/2011 | Rached |
| 8,246,850 | B2 | 8/2012 | Rached |
| 8,252,198 | B2 | 8/2012 | Rached |
| 8,450,537 | B2 | 5/2013 | Rao et al. |
| 8,557,135 | B2 | 10/2013 | Rached |
| 8,808,569 | B2 | 8/2014 | Rached |
| 8,858,824 | B2 | 10/2014 | Boussand |
| 8,858,825 | B2 | 10/2014 | Guerin et al. |
| 9,011,711 | B2 | 4/2015 | Rached |
| 9,028,706 | B2 | 5/2015 | Rached et al. |
| 9,039,922 | B2 | 5/2015 | Rached |
| 9,127,191 | B2 | 9/2015 | Rached |
| 9,133,379 | B2 | 9/2015 | Rached |
| 9,175,203 | B2 | 11/2015 | Rached |
| 9,267,064 | B2 | 2/2016 | Rached |
| 9,315,708 | B2 | 4/2016 | Guerin et al. |
| 9,399,726 | B2 | 7/2016 | Rached |
| 9,505,968 | B2 | 11/2016 | Rached |
| 9,512,343 | B2 | 12/2016 | Rached et al. |
| 9,599,381 | B2 | 3/2017 | Rached |
| 9,650,551 | B2 | 5/2017 | Collier et al. |
| 9,650,553 | B2 | 5/2017 | Deur-Bert et al. |
| 9,663,697 | B2 | 5/2017 | Rached |
| 9,676,984 | B2 | 6/2017 | Guerin et al. |
| 9,683,155 | B2 | 6/2017 | Deur-Bert et al. |
| 9,683,157 | B2 | 6/2017 | Rached |
| 9,884,984 | B2 | 2/2018 | Rached |
| 9,889,416 | B2 | 2/2018 | Bonnet et al. |
| 9,908,828 | B2 | 3/2018 | Rached et al. |
| 9,969,918 | B2 | 5/2018 | Deur-Bert et al. |
| 10,023,780 | B2 | 7/2018 | Guerin et al. |
| 10,029,963 | B2 | 7/2018 | Bonnet et al. |
| 10,035,938 | B2 | 7/2018 | Rached |
| 10,077,221 | B2 | 9/2018 | Bonnet et al. |
| 10,119,055 | B2 | 11/2018 | Boussand |
| 10,125,296 | B2 | 11/2018 | Rached |
| 10,131,829 | B2 | 11/2018 | Deur-Bert et al. |
| 10,252,913 | B2 | 4/2019 | Bonnet et al. |
| 10,266,465 | B2 | 4/2019 | Bonnet et al. |

(Continued)

FOREIGN PATENT DOCUMENTS

| CN | 102295522 A | 12/2011 |
|---|---|---|
| WO | 2007053736 A2 | 5/2007 |

(Continued)

OTHER PUBLICATIONS

International Search Report (PCT/ISA/210) dated May 22, 2019, by the French Patent Office as the International Searching Authority for International Application No. PCT/FR2019/050229.
Written Opinion (PCT/ISA/237) dated May 22, 2019, by the French Patent Office as the International Searching Authority for International Application No. PCT/FR2019/050229.
U.S. Appl. No. 17/147,202, Rached et al.
U.S. Appl. No. 17/164,888, Rached.
\*\*Rached, Wissam, et al., U.S. Appl. No. 17/147,202 entitled "Composition Based on 2,3,3,3-Tetrafluoropropene," filed in the U.S. Patent and Trademark Office filed Jan. 12, 2021.

(Continued)

*Primary Examiner* — Jafar F Parsa
(74) *Attorney, Agent, or Firm* — Buchanan Ingersoll & Rooney P.C.

(57) ABSTRACT

The present invention relates to an azeotropic or quasi-azeotropic composition comprising hydrogen fluoride, 2,3,3,3-tetrafluoropropene and 1,1,1,2,2-pentafluoropropane, characterized in that said composition has a boiling point above 40° C.

12 Claims, No Drawings

(56) References Cited

U.S. PATENT DOCUMENTS

| | | |
|---|---|---|
| 10,316,231 B2 | 6/2019 | Rached |
| 10,343,963 B2 | 7/2019 | Bonnet et al. |
| 10,358,592 B2 | 7/2019 | Rached |
| 10,377,935 B2 | 8/2019 | Guerin et al. |
| 10,399,918 B2 | 9/2019 | Rached |
| 10,450,488 B2 | 10/2019 | Boussand |
| 10,596,536 B2 | 3/2020 | Bonnet et al. |
| 10,604,690 B2 | 3/2020 | Collier et al. |
| 10,618,861 B2 | 4/2020 | Rached |
| 10,662,357 B2 | 5/2020 | Boussand |
| 10,808,157 B2 | 10/2020 | Rached |
| 10,858,562 B2 | 12/2020 | Rached |
| 2007/0100173 A1 | 5/2007 | Miller et al. |
| 2007/0100175 A1 | 5/2007 | Miller et al. |
| 2008/0051612 A1 | 2/2008 | Knapp |
| 2009/0127496 A1 | 5/2009 | Rao et al. |
| 2009/0224207 A1 | 9/2009 | Pham et al. |
| 2010/0072415 A1 | 3/2010 | Rao |
| 2010/0187088 A1 | 7/2010 | Merkel et al. |
| 2010/0237279 A1 | 9/2010 | Hulse et al. |
| 2011/0084228 A1 | 4/2011 | Rached |
| 2011/0095224 A1 | 4/2011 | Rached |
| 2011/0112340 A1 | 5/2011 | Smith et al. |
| 2011/0186772 A1 | 8/2011 | Rached |
| 2011/0218369 A1 | 9/2011 | Elsheikh et al. |
| 2011/0219791 A1 | 9/2011 | Rached |
| 2011/0219792 A1 | 9/2011 | Rached |
| 2011/0240254 A1 | 10/2011 | Rached |
| 2011/0284181 A1 | 11/2011 | Rached |
| 2012/0041239 A1 | 2/2012 | Suzuki et al. |
| 2012/0049104 A1 | 3/2012 | Rached |
| 2012/0053369 A1 | 3/2012 | Hulse et al. |
| 2012/0056122 A1 | 3/2012 | Hulse et al. |
| 2012/0056123 A1 | 3/2012 | Rached |
| 2012/0068105 A1 | 3/2012 | Rached et al. |
| 2012/0138841 A1 | 6/2012 | Hulse et al. |
| 2012/0144857 A1 | 6/2012 | Rached |
| 2012/0151958 A1 | 6/2012 | Rached |
| 2012/0151959 A1 | 6/2012 | Rached |
| 2012/0153213 A1 | 6/2012 | Rached |
| 2012/0159982 A1 | 6/2012 | Rached |
| 2012/0161064 A1 | 6/2012 | Rached |
| 2012/0167615 A1 | 7/2012 | Rached |
| 2012/0205574 A1 | 8/2012 | Rached et al. |
| 2012/0222448 A1 | 9/2012 | Chaki et al. |
| 2013/0092869 A1 | 4/2013 | Boussand |
| 2013/0102814 A1 | 4/2013 | Rao et al. |
| 2013/0105296 A1 | 5/2013 | Chaki et al. |
| 2013/0105724 A1 | 5/2013 | Boussand |
| 2013/0186114 A1 | 7/2013 | Guerin et al. |
| 2014/0008565 A1 | 1/2014 | Rached et al. |
| 2014/0012052 A1 | 1/2014 | Pham et al. |
| 2014/0075969 A1 | 3/2014 | Guerin et al. |
| 2014/0318160 A1 | 10/2014 | Rached |
| 2014/0326017 A1 | 11/2014 | Rached |
| 2015/0027146 A1 | 1/2015 | Boussand |
| 2015/0152306 A1 | 6/2015 | Rached |
| 2015/0152307 A1 | 6/2015 | Rached |
| 2015/0322317 A1 | 11/2015 | Collier et al. |
| 2015/0322321 A1 | 11/2015 | Deur-Bert et al. |
| 2015/0344761 A1 | 12/2015 | Rached |
| 2015/0353799 A1 | 12/2015 | Deur-Bert et al. |
| 2015/0353802 A1 | 12/2015 | Rached |
| 2016/0009555 A1* | 1/2016 | Bonnet .............. C01B 7/191 252/182.12 |
| 2016/0024363 A1 | 1/2016 | Rached |
| 2016/0025394 A1 | 1/2016 | Rached |
| 2016/0046548 A1 | 2/2016 | Bonnet et al. |
| 2016/0115361 A1 | 4/2016 | Boussand |
| 2016/0122609 A1 | 5/2016 | Rached |
| 2016/0194541 A1 | 7/2016 | Guerin et al. |
| 2016/0244652 A1 | 8/2016 | Rached |
| 2016/0272561 A1 | 9/2016 | Rached et al. |
| 2016/0298014 A1 | 10/2016 | Rached |
| 2016/0355718 A1 | 12/2016 | Rached |
| 2016/0376484 A1 | 12/2016 | Guerin et al. |
| 2017/0037291 A1 | 2/2017 | Rached et al. |
| 2017/0080773 A1 | 3/2017 | Rached |
| 2017/0145276 A1 | 5/2017 | Rached |
| 2017/0210960 A1 | 7/2017 | Deur-Bert et al. |
| 2017/0210962 A1 | 7/2017 | Collier et al. |
| 2017/0218241 A1 | 8/2017 | Deur-Bert et al. |
| 2017/0218242 A1 | 8/2017 | Rached |
| 2018/0086173 A1 | 3/2018 | Rached |
| 2018/0134936 A1 | 5/2018 | Rached |
| 2018/0148395 A1 | 5/2018 | Rached et al. |
| 2018/0244970 A1 | 8/2018 | Rached |
| 2018/0282603 A1 | 10/2018 | Guerin et al. |
| 2018/0327645 A1 | 11/2018 | Boussand |
| 2019/0023957 A1 | 1/2019 | Rached |
| 2019/0203094 A1 | 7/2019 | Rached |
| 2019/0249057 A1 | 8/2019 | Rached |
| 2019/0284500 A1 | 9/2019 | Rached |
| 2019/0337874 A1 | 11/2019 | Rached et al. |
| 2019/0359870 A1 | 11/2019 | Rached |
| 2019/0367789 A1 | 12/2019 | Rached |
| 2020/0048518 A1 | 2/2020 | Rached |
| 2020/0216734 A1 | 7/2020 | Rached et al. |
| 2020/0407613 A1 | 12/2020 | Rached |
| 2021/0046802 A1 | 2/2021 | Rached |

FOREIGN PATENT DOCUMENTS

| | | | |
|---|---|---|---|
| WO | WO 2008/002500 A1 | 1/2008 | |
| WO | 2008/054781 A1 | 5/2008 | |
| WO | 2009105512 A1 | 8/2009 | |
| WO | WO 2009/105517 A2 | 8/2009 | |
| WO | 2010059493 A1 | 5/2010 | |
| WO | 2011010025 A1 | 1/2011 | |
| WO | WO 2012/075283 A2 | 6/2012 | |
| WO | 2013088195 A1 | 6/2013 | |
| WO | 2014147310 A1 | 9/2014 | |

OTHER PUBLICATIONS

**Rached, Wissam, U.S. Appl. No. 17/164,888 entitled "Use of Tetrafluoropropene Based Compositions," filed in the U.S. Patent and Trademark Office filed Feb. 2, 2021.

* cited by examiner

TERNARY AZEOTROPIC OR QUASI-AZEOTROPIC COMPOSITION COMPRISING HF, 2,3,3,3-TETRAFLUOROPROPENE AND 1,1,1,2,2-PENTAFLUOROPROPANE

TECHNICAL FIELD OF THE INVENTION

The present invention relates to a composition comprising hydrogen fluoride, 2,3,3,3-tetrafluoropropene and 1,1,1,2,2-pentafluoropropene. In particular, the present invention relates to an azeotropic or quasi-azeotropic composition comprising hydrogen fluoride, 2,3,3,3-tetrafluoropropene and 1,1,1,2,2-pentafluoropropene.

TECHNOLOGICAL BACKGROUND OF THE INVENTION

Hydrofluorocarbons (HFC) and in particular hydrofluoroolefins, such as 2,3,3,3-tetrafluoro-1-propene (HFO 1234yf) are compounds known for their properties as refrigerants and heat-transfer fluids, extinguishers, propellants, foaming agents, swelling agents, dielectric gases, polymerization medium or monomer, support fluids, abrasive agents, drying agents and fluids for power production units. Unlike CFCs and HCFCs, which are potentially hazardous to the ozone layer, HFOs do not contain any chlorine and thus do not pose any problems for the ozone layer. Several processes for manufacturing 1234yf are known. For example, WO 2011/010025 describes the process for preparing 2,3,3,3-tetrafluoropropene from hexafluoropropylene. The preparation of 2,3,3,3-tetrafluoropropene from 1,1,1,2,3-pentachloropropane is also known from WO 2013/088195 In addition to the reaction steps per se, the processes for preparing 2,3,3,3-tetrafluoropropene that are known from the prior art carry out one or more purification steps generally including one or more distillations.

The operation of a distillation column can be disrupted by the formation of azeotropic compositions during the use of said column. This can cause a decrease in efficiency in the separation of the various compounds. This can also cause a poor design of the distillation column with significant repercussions on the overall efficiency of the process of the industrial scale. The existence of azeotropes between hydrogen fluoride and 2,3,3,3-tetrafluoropropene is known from U.S. Pat. No. 7,476,771. In addition, the existence of azeotropes between hydrogen fluoride and 1,1,1,2,2-pentafluoropropane, a byproduct observed in processes for preparing 2,3,3,3-tetrafluoropropene, is also known from WO 2008/054781.

The identification of new azeotropic compositions is essential for providing an efficient separation or purification process.

SUMMARY OF THE INVENTION

According to a first aspect, the present invention relates to an azeotropic or quasi-azeotropic composition comprising hydrogen fluoride, 2,3,3,3-tetrafluoropropene and 1,1,1,2,2-pentafluoropropane, characterized in that said composition has a boiling point above 40° C., advantageously above 45° C., preferably above 50° C.

According to one preferred embodiment, said composition is obtained for a pressure greater than 11 bara, advantageously greater than 13 bara, preferably greater than 15 bara.

According to one preferred embodiment, said composition has a boiling point of between 40° C. and 100° C. at a pressure of between 11 and 30 bara; advantageously a boiling point of between 45° C. and 100° C. at a pressure of between 13 and 30 bara.

According to one preferred embodiment, the hydrogen fluoride content is from 10 to 70 mol %, on the basis of the molar composition of said composition.

According to one preferred embodiment, the 2,3,3,3-tetrafluoropropene content is from 10 to 90 mol %, on the basis of the molar composition of said composition.

According to one preferred embodiment, the 1,1,1,2,2-pentafluoropropane content is from 1 to 50 mol %, on the basis of the molar composition of said composition.

According to one preferred embodiment, the boiling point of said azeotropic or quasi-azeotropic composition is between 45° C. and 65° C. at a pressure of between 13 and 20 bara, advantageously between 50° C. and 65° C. at a pressure between 15 and 20 bara.

According to one preferred embodiment, said azeotropic or quasi-azeotropic composition consists of hydrogen fluoride, 2,3,3,3-tetrafluoropropene and 1,1,1,2,2-pentafluoropropane.

According to one preferred embodiment, the azeotropic or quasi-azeotropic composition comprises 31 mol % of hydrogen fluoride, 66 mol % of 2,3,3,3-tetrafluoropropene and 3 mol % de 1,1,1,2,2-pentafluoropropane, and has a boiling point of 60° C. at a pressure of 18 bara.

According to a second aspect, the present invention relates to a process for separating a composition comprising hydrogen fluoride, 2,3,3,3-tetrafluoropropene and 1,1,1,2,2-pentafluoropropane, characterized in that it comprises the steps of:
i) providing a composition comprising hydrogen fluoride, 2,3,3,3-tetrafluoropropene and 1,1,1,2,2-pentafluoropropane;
ii) distilling said composition provided in step i) at a temperature at the bottom of the distillation column below 45° C., preferably below 40° C., so as to form and recover a first stream, advantageously at the top of the distillation column, comprising 2,3,3,3-tetrafluoropropene and hydrogen fluoride, and a second stream, advantageously at the bottom of the distillation column, comprising 1,1,1,2,2-pentafluoropropane and hydrogen fluoride.

The implementation of the process according to the second aspect of the present invention makes it possible to prevent the formation of the ternary azeotropic composition according to the present invention, and thus to efficiently separate the 2,3,3,3-tetrafluoropropene from the 1,1,1,2,2-pentafluoropropane by distillation.

DETAILED DESCRIPTION OF THE INVENTION

According to a first aspect of the present invention, an azeotropic or quasi-azeotropic composition is provided. Preferably, said azeotropic or quasi-azeotropic composition comprises hydrogen fluoride, 2,3,3,3-tetrafluoropropene and 1,1,1,2,2-pentafluoropropane.

The applicant has identified, surprisingly, the formation of an HF/HFO-1234yf/HFC-245cb ternary azeotropic composition under particular temperature conditions. The formation of this ternary composition during steps for distillation of a reaction stream can disrupt the correct operation of said steps and prevent efficient separation between 2,3,3,3-tetrafluoropropene and 1,1,1,2,2-pentafluoropropane when such a separation is desired.

Preferably, said azeotropic or quasi-azeotropic composition comprises hydrogen fluoride, 2,3,3,3-tetrafluoropropene and 1,1,1,2,2-pentafluoropropane and has a boiling point above 40° C. In particular, said azeotropic or quasi-azeotropic composition has a boiling point above 41° C. or above 42° C. or above 43° C. or above 44° C. or above 45° C. or above 46° C. or above 47° C. or above 48° C. or above 49° C. or above 50° C.

In particular, said azeotropic or quasi-azeotropic composition has a boiling point below 100° C., advantageously below 90° C., preferably below 80° C., in particular below 70° C. Thus, said azeotropic or quasi-azeotropic composition has a boiling point below 100° C. or below 99° C. or below 98° C. or below 97° C. or below 96° C. or below 95° C. or below 94° C. or below 93° C. or below 92° C. or below 91° C. or below 90° C. or below 89° C. or below 88° C. or below 87° C. or below 86° C. or below 85° C. or below 84° C. or below 83° C. or below 82° C. or below 81° C. or below 80° C. or below 79° C. or below 78° C. or below 77° C. or below 76° C. or below 75° C. or below 74° C. or below 73° C. or below 72° C. or below 71° C. or below 70° C.

More preferentially, said azeotropic or quasi-azeotropic composition has a boiling point below 69° C. or below 68° C. or below 67° C. or below 66° C. or below 65° C.

Preferably, said azeotropic or quasi-azeotropic composition has a boiling point above 40° C. or above 41° C. or above 42° C. or above 43° C. or above 44° C. or above 45° C. or above 46° C. or above 47° C. or above 48° C. or above 49° C. or above 50° C.; and below 100° C., advantageously below 90° C., preferably below 80° C., in particular below 70° C.

In particular, said azeotropic or quasi-azeotropic composition has a boiling point above 40° C. or above 41° C. or above 42° C. or above 43° C. or above 44° C. or above 45° C. or above 46° C. or above 47° C. or above 48° C. or above 49° C. or above 50° C.; and below 100° C. or below 99° C. or below 98° C. or below 97° C. or below 96° C. or below 95° C. or below 94° C. or below 93° C. or below 92° C. or below 91° C. or below 90° C. or below 89° C. or below 88° C. or below 87° C. or below 86° C. or below 85° C. or below 84° C. or below 83° C. or below 82° C. or below 81° C. or below 80° C. or below 79° C. or below 78° C. or below 77° C. or below 76° C. or below 75° C. or below 74° C. or below 73° C. or below 72° C. or below 71° C. or below 70° C.

More particularly, said azeotropic or quasi-azeotropic composition has a boiling point above 40° C. or above 41° C. or above 42° C. or above 43° C. or above 44° C. or above 45° C. or above 46° C. or above 47° C. or above 48° C. or above 49° C. or above 50° C.; and below 69° C., or below 68° C., or below 67° C., or below 66° C. or below 65° C.

In particular, said azeotropic or quasi-azeotropic composition has a boiling point of between 45° C. and 65° C. More particularly, said azeotropic or quasi-azeotropic composition has a boiling point of between 50° C. and 65° C.

According to one preferred embodiment, the azeotropic or quasi-azeotropic composition is obtained for a pressure of between 11 and 30 bara, advantageously between 11 and 25 bara, preferably between 11 and 24 bara, more preferentially between 12 and 23 bara, in particular between 12 and 22 bara, more particularly between 12 and 21 bara, preferably between 12 and 20 bara, more preferably between 13 and 20 bara.

Preferably, said azeotropic or quasi-azeotropic composition comprises hydrogen fluoride, 2,3,3,3-tetrafluoropropene and 1,1,1,2,2-pentafluoropropane and has a boiling point of between 40° C. and 100° C. at a pressure of between 11 and 30 bara, advantageously a boiling point between 45° C. and 90° C. at a pressure of between 13 and 28 bara, preferably a boiling point between 45° C. and 80° at a pressure of between 13 and 25 bara, more preferentially a boiling point between 45° C. and 70° C. at a pressure of between 13 and 21 bara, in particular a boiling point between 45° C. and 65° C. at a pressure of between 13 and 20 bara, more particularly a boiling point between 50° C. and 65° C. at a pressure of between 15 and 20 bara.

According to one preferred embodiment, the hydrogen fluoride content is from 10 to 70 mol %, on the basis of the molar composition of said composition, preferably from 15 to 65 mol %, in particular from 20 to 60 mol %, more particularly from 25 to 55 mol %, on the basis of the molar composition of said composition According to one preferred embodiment, the 2,3,3,3-tetrafluoropropene content is from 10 to 90 mol %, on the basis of the molar composition of said composition, preferably from 15 to 85 mol %, in particular from 20 to 80 mol %, more particularly from 20 to 75 mol %, preferably from 20 to 70 mol %, on the basis of the molar composition of said composition According to one preferred embodiment, the 1,1,1,2,2-pentafluoropropane content is from 1 to 50 mol %, on the basis of the molar composition of said composition, preferably from 1 to 45 mol %, in particular from 1 to 40 mol %, more particularly from 2 to 35 mol %, preferably from 2 to 30 mol %, on the basis of the molar composition of said composition According to one preferred embodiment, the azeotropic or quasi-azeotropic composition comprises hydrogen fluoride, 2,3,3,3-tetrafluoropropene and 1,1,1,2,2-pentafluoropropane; the hydrogen fluoride content is from 10 to 70 mol %, on the basis of the molar composition of said composition, preferably from 15 to 65 mol %, in particular from 20 to 60 mol %, more particularly from 25 to 55 mol %, on the basis of the molar composition of said composition, and said composition has a boiling point of between 40° C. and 100° C. at a pressure of between 11 and 30 bara, advantageously a boiling point between 45° C. and 90° C. at a pressure of between 13 and 28 bara, preferably a boiling point between 45° C. and 80° at a pressure of between 13 and 25 bara, more preferentially a boiling point between 45° C. and 70° C. at a pressure of between 13 and 21 bara, in particular a boiling point between 45° C. and 65° C. at a pressure of between 13 and 20 bara, more particularly a boiling point between 50° C. and 65° C. at a pressure of between 15 and 20 bara.

According to one preferred embodiment, the azeotropic or quasi-azeotropic comprises hydrogen fluoride, 2,3,3,3-tetrafluoropropene and 1,1,1,2,2-pentafluoropropane; the 2,3,3,3-tetrafluoropropene content is from 10 to 90 mol %, on the basis of the molar composition of said composition, preferably from 15 to 85 mol %, in particular from 20 to 80 mol %, more particularly from 20 to 75 mol %, preferably from 20 to 70 mol %, on the basis of the molar composition of said composition; and said composition has a boiling point of between 40° C. and 100° C. at a pressure of between 11 and 30 bara, advantageously a boiling point between 45° C. and 90° C. at a pressure of between 13 and 28 bara, preferably a boiling point between 45° C. and 80° at a pressure of between 13 and 25 bara, more preferentially a boiling point between 45° C. and 70° C. at a pressure of between 13 and 21 bara, in particular a boiling point between 45° C. and 65° C. at a pressure of between 13 and 20 bara, more particularly a boiling point between 50° C. and 65° C. at a pressure of between 15 and 20 bara.

According to one preferred embodiment, the azeotropic or quasi-azeotropic comprises hydrogen fluoride, 2,3,3,3-tetrafluoropropene and 1,1,1,2,2-pentafluoropropane; the 1,1,1,2,2-pentafluoropropane content is from 1 to 50 mol %, on the basis of the molar composition of said composition, preferably from 1 to 45 mol %, in particular from 1 to 40 mol %, more particularly from 2 to 35 mol %, preferably from 2 to 30 mol %, on the basis of the molar composition of said composition; and said composition has a boiling point of between 40° C. and 100° C. at a pressure of between 11 and 30 bara, advantageously a boiling point between 45° C. and 90° C. at a pressure of between 13 and 28 bara, preferably a boiling point between 45° C. and 80° at a pressure of between 13 and 25 bara, more preferentially a boiling point between 45° C. and 70° C. at a pressure of between 13 and 21 bara, in particular a boiling point between 45° C. and 65° C. at a pressure of between 13 and 20 bara, more particularly a boiling point between 50° C. and 65° C. at a pressure of between 15 and 20 bara.

According to one preferred embodiment, the azeotropic or quasi-azeotropic composition comprises hydrogen fluoride, 2,3,3,3-tetrafluoropropene and 1,1,1,2,2-pentafluoropropane; the hydrogen fluoride content is from 10 to 70 mol %, on the basis of the molar composition of said composition, preferably from 15 to 65 mol %, in particular from 20 to 60 mol %, more particularly from 25 to 55 mol % on the basis of the molar composition of said composition; the 2,3,3,3-tetrafluoropropene content is from 10 to 90 mol %, on the basis of the molar composition of said composition, preferably from 15 to 85 mol %, in particular from 20 to 80 mol %, more particularly from 20 to 75 mol %, preferably from 20 to 70 mol %, on the basis of the molar composition of said composition; and said composition has a boiling point of between 40° C. and 100° C. at a pressure of between 11 and 30 bara, advantageously a boiling point between 45° C. and 90° C. at a pressure of between 13 and 28 bara, preferably a boiling point between 45° C. and 80° at a pressure of between 13 and 25 bara, more preferentially a boiling point between 45° C. and 70° C. at a pressure of between 13 and 21 bara, in particular a boiling point between 45° C. and 65° C. at a pressure of between 13 and 20 bara, more particularly a boiling point between 50° C. and 65° C. at a pressure of between 15 and 20 bara.

According to one preferred embodiment, the azeotropic or quasi-azeotropic composition comprises hydrogen fluoride, 2,3,3,3-tetrafluoropropene and 1,1,1,2,2-pentafluoropropane; the hydrogen fluoride content is from 10 to 70 mol %, on the basis of the molar composition of said composition, preferably from 15 to 65 mol %, in particular from 20 to 60 mol %, more particularly from 25 to 55 mol % on the basis of the molar composition of said composition; the 1,1,1,2,2-pentafluoropropane content is from 1 to 50 mol %, on the basis of the molar composition of said composition, preferably from 1 to 45 mol %, in particular from 1 to 40 mol %, more particularly from 2 to 35 mol %, preferably from 2 to 30 mol %, on the basis of the molar composition of said composition; and said composition has a boiling point of between 40° C. and 100° C. at a pressure of between 11 and 30 bara, advantageously a boiling point between 45° C. and 90° C. at a pressure of between 13 and 28 bara, preferably a boiling point between 45° C. and 80° at a pressure of between 13 and 25 bara, more preferentially a boiling point between 45° C. and 70° C. at a pressure of between 13 and 21 bara, in particular a boiling point between 45° C. and 65° C. at a pressure of between 13 and 20 bara, more particularly a boiling point between 50° C. and 65° C. at a pressure of between 15 and 20 bara.

According to one preferred embodiment, the azeotropic or quasi-azeotropic composition comprises hydrogen fluoride, 2,3,3,3-tetrafluoropropene and 1,1,1,2,2-pentafluoropropane; the 2,3,3,3-tetrafluoropropene content is from 10 to 90 mol %, on the basis of the molar composition of said composition, preferably from 15 to 85 mol %, in particular from 20 to 80 mol %, more particularly from 20 to 70 mol %, preferably from 20 to 70 mol %, on the basis of the molar composition of said composition; the 1,1,1,2,2-pentafluoropropane content is from 1 to 50 mol %, on the basis of the molar composition of said composition, preferably from 1 to 45 mol %, in particular from 1 to 40 mol %, more particularly from 2 to 35 mol %, preferably from 2 to 30 mol %, on the basis of the molar composition of said composition; and said composition has a boiling point of between 40° C. and 100° C. at a pressure of between 11 and 30 bara, advantageously a boiling point between 45° C. and 90° C. at a pressure of between 13 and 28 bara, preferably a boiling point between 45° C. and 80° at a pressure of between 13 and 25 bara, more preferentially a boiling point between 45° C. and 70° C. at a pressure of between 13 and 21 bara, in particular a boiling point between 45° C. and 65° C. at a pressure of between 13 and 20 bara, more particularly a boiling point between 50° C. and 65° C. at a pressure of between 15 and 20 bara.

Preferably, said azeotropic or quasi-azeotropic composition comprises from 10 to 70 mol % of hydrogen fluoride, from 10 to 90 mol % of 2,3,3,3-tetrafluoropropene and from 1 to 50 mol % of 1,1,1,2,2-pentafluoropropane, on the basis of the molar composition of said composition.

In particular, said azeotropic or quasi-azeotropic composition comprises from 10 to 70 mol %, preferably from 15 to 65 mol %, in particular from 20 to 60 mol %, more particularly from 25 to 55 mol % of hydrogen fluoride; from 10 to 90 mol %, preferably from 15 to 85 mol %, in particular from 20 to 80 mol %, more particularly from 20 to 75 mol %, preferably from 20 to 70 mol % of 2,3,3,3-tetrafluoropropene; and from 1 to 50 mol %, preferably from 1 to 45 mol %, in particular from 1 to 40 mol %, more particularly from 2 to 35 mol %, preferably from 2 to 30 mol % of 1,1,1,2,2-pentafluoropropane, on the basis of the molar composition of said composition.

More particularly, said composition consists of:
from 10 to 70 mol %, preferably from 15 to 65 mol %, in particular from 20 to 60 mol %, more particularly from 25 to 55 mol % of hydrogen fluoride;
from 10 to 90 mol %, preferably from 15 to 85 mol %, in particular from 20 to 80 mol %, more particularly from 20 to 75 mol %, preferably from 20 to 70 mol % of 2,3,3,3-tetrafluoropropene; and
from 1 to 50 mol %, preferably from 1 to 45 mol %, in particular from 1 to 40 mol %, more particularly from 2 to 35 mol %, preferably from 2 to 30 mol % of 1,1,1,2,2-pentafluoropropane,
on the basis of the molar composition of said composition.

Thus, in one particularly preferred embodiment, the present invention provides an azeotropic or quasi-azeotropic composition comprising:
from 10 to 70 mol %, preferably from 15 to 65 mol %, in particular from 20 to 60 mol %, more particularly from 25 to 55 mol % of hydrogen fluoride;
from 10 to 90 mol %, preferably from 15 to 85 mol %, in particular from 20 to 80 mol %, more particularly from 20 to 75 mol %, preferably from 20 to 70 mol % of 2,3,3,3-tetrafluoropropene; and from 1 to 50 mol %, preferably from 1 to 45 mol %, in particular from 1 to 40 mol %, more particularly from 2 to 35 mol %, preferably from 2 to 30 mol % of 1,1,1,2,2-pentafluoropropane, on the basis of the molar composition of said composition; said composition having a boiling point of between 40° C. and 100° C. at a pressure of between 11 and 30 bara, advantageously a boiling point between 45° C. and 90° C. at a pressure of between 13 and 28 bara, preferably a boiling point between 45° C. and 80° at a pressure of between 13 and 25 bara, more preferentially a boiling point between 45° C. and 70° C. at a pressure of between 13 and 21 bara, in particular a boiling point between 45° C. and 65° C. at a pressure of between 13 and 20 bara, more particularly a boiling point between 50° C. and 65° C. at a pressure of between 15 and 20 bara.

In particular, the present invention provides an azeotropic or quasi-azeotropic composition consisting of:

from 10 to 70 mol %, preferably from 15 to 65 mol %, in particular from 20 to 60 mol %, more particularly from 25 to 55 mol % of hydrogen fluoride;

from 10 to 90 mol %, preferably from 15 to 85 mol %, in particular from 20 to 80 mol %, more particularly from 20 to 75 mol %, preferably from 20 to 70 mol % of 2,3,3,3-tetrafluoropropene; and from 1 to 50 mol %, preferably from 1 to 45 mol %, in particular from 1 to 40 mol %, more particularly from 2 to 35 mol %, preferably from 2 to 30 mol % of 1,1,1,2,2-pentafluoropropane, on the basis of the molar composition of said composition; said composition having a boiling point of between 45° C. and 65° C. at a pressure of between 13 and 20 bara; advantageously a boiling point of between 50° C. and 65° C. at a pressure between 15 and 20 bara.

Preferably, the azeotropic composition comprises, preferably consists of, 31 mol % hydrogen fluoride, 66 mol % 2,3,3,3-tetrafluoropropene and 3 mol % 1,1,1,2,2-pentafluoropropane, and has a boiling point of 60° C. at a pressure of 18 bara.

According to a second aspect, a process for separating a composition comprising hydrogen fluoride, 2,3,3,3-tetrafluoropropene and 1,1,1,2,2-pentafluoropropane is provided. Said process comprises the steps of:

i) providing a composition comprising hydrogen fluoride, 2,3,3,3-tetrafluoropropene and 1,1,1,2,2-pentafluoropropane;

ii) distilling said composition provided in step i) at a temperature at the bottom of the distillation column below 45° C., preferably below 40° C., so as to form and recover a first stream, advantageously at the top of the distillation column, comprising 2,3,3,3-tetrafluoropropene and hydrogen fluoride, and a second stream, advantageously at the bottom of the distillation column, comprising 1,1,1,2,2-pentafluoropropane and hydrogen fluoride.

Advantageously, said first stream comprises at least 90%, preferably at least 95%, more preferentially at least 98%, in particular at least 99% of the 2,3,3,3-tetrafluoropropene present in said composition of step i).

Advantageously, said first stream comprises less than 40%, preferably less than 30%, more preferentially less than 20%, in particular less than 15%, more particularly less than 10%, preferably less than 5% of the 1,1,1,2,2-pentafluoropropane present in said composition of step i).

Preferably, step ii) is carried out at a temperature at the bottom of the distillation column above −5° C., advantageously above 0° C., preferably above 5° C.

Preferably, step ii) is carried out at a temperature at the bottom of the distillation column below 45° C., preferably below 40° C., and above −5° C., advantageously above 0° C., preferably above 5° C.

EXAMPLE

At 60° C. and 18 bara, the composition comprising 31 mol % of HF, 66 mol % of HFO-1234yf and 3 mol % of HFC-245cb was identified as azeotropic.

The invention claimed is:

1. An azeotropic or quasi-azeotropic composition comprising hydrogen fluoride, 2,3,3,3-tetrafluoropropene and 1,1,1,2,2-pentafluoropropane, wherein said composition has a boiling point between 45° C. and 100° C. at a pressure of 13 to 30 bara.

2. The composition as claimed in claim 1, wherein the composition is obtained for a pressure greater than 15 bara.

3. The composition as claimed in claim 1, wherein the composition has a boiling point of between 45° C. and 90° C. at a pressure of between 13 and 28 bara.

4. The composition as claimed in claim 1, wherein the hydrogen fluoride content is from 10 to 70 mol %, on the basis of the molar composition of said composition.

5. The composition as claimed in claim 1, wherein the 2,3,3,3-tetrafluoropropene content is from 10 to 90 mol %, on the basis of the molar composition of said composition.

6. The composition as claimed in claim 1, wherein the 1,1,1,2,2-pentafluoropropane content is from 1 to 50 mol %, on the basis of the molar composition of said composition.

7. The composition as claimed in claim 1, wherein the boiling point of said azeotropic or quasi-azeotropic composition is between 45° C. and 65° C. at a pressure of between 13 and 20 bara.

8. The composition as claimed in claim 1, wherein the composition comprises 31 mol % hydrogen fluoride, 66 mol % 2,3,3,3-tetrafluoropropene and 3 mol % 1,1,1,2,2-pentafluoropropane, and has a boiling point of 60° C. at a pressure of 18 bara.

9. The composition as claimed in claim 1, wherein the composition consists of hydrogen fluoride, 2,3,3,3-tetrafluoropropene and 1,1,1,2,2-pentafluoropropane.

10. A process for separating a composition comprising hydrogen fluoride, 2,3,3,3-tetrafluoropropene and 1,1,1,2,2-pentafluoropropane, wherein the process comprises the steps of:

i) providing a composition comprising hydrogen fluoride, 2,3,3,3-tetrafluoropropene and 1,1,1,2,2-pentafluoropropane;

ii) distilling said composition provided in step i) at a temperature at the bottom of the distillation column below 45° C., and above 0° C., so as to form and recover a first stream, advantageously at the top of the distillation column, comprising 2,3,3,3-tetrafluoropropene and hydrogen fluoride, and a second stream comprising 1,1,1,2,2-pentafluoropropane and hydrogen fluoride; said first stream comprises at least 90% of the 2,3,3,3-tetrafluoropropene present in said composition of step i).

11. The process as claimed in claim 10, wherein said first stream comprises at least 95% of the 2,3,3,3-tetrafluoropropene present in said composition of step i).

12. The process as claimed in claim 11, wherein said first stream comprises less than 40% of the 1,1,1,2,2-pentafluoropropane present in said composition of step i).

* * * * *